US00PP34938P2

(12) United States Plant Patent
Rietberg

(10) Patent No.: US PP34,938 P2
(45) Date of Patent: Jan. 24, 2023

(54) ***HEBE* PLANT NAMED 'HM150255'**

(50) Latin Name: ***Hebe* hybrid**
Varietal Denomination: HM150255

(71) Applicant: Henrik Christiaan Cozijn Rietberg, Wezep (NL)

(72) Inventor: Henrik Christiaan Cozijn Rietberg, Wezep (NL)

(73) Assignee: EDEN'S CREATIONS B.V., Wezep (NL)

( * ) Notice: Subject to any disclaimer, the term of this patent is extended or adjusted under 35 U.S.C. 154(b) by 0 days.

(21) Appl. No.: 17/744,104

(22) Filed: May 13, 2022

(51) Int. Cl.
*A01H 5/02* (2018.01)
*A01H 6/68* (2018.01)

(52) U.S. Cl.
USPC ..... Plt./251
CPC ..... *A01H 6/68* (2018.05)

(58) Field of Classification Search
USPC ..... Plt./251
CPC ..... A01H 6/68
See application file for complete search history.

*Primary Examiner* — Anne Marie Grunberg
(74) *Attorney, Agent, or Firm* — Penny J. Aguirre

(57) ABSTRACT

A new cultivar of *Hebe* plant named 'HM150255' that is characterized by its consistently healthy plants that have a low susceptibility to leaf spot disease and downy mildew, its strong stems, its leaves that are small in size, its flowers that are self-cleaning, its flowers that are lavender-violet in color, and its floriferous blooming habit.

2 Drawing Sheets

Botanical classification: *Hebe* hybrid.
Cultivar designation: 'HM150255'.

CROSS REFERENCE TO A RELATED APPLICATION

This application is related to a European plant breeders' rights application filed on Sep. 15, 2020, application No. 2020/2163. The Applicant received the information for the Plant breeders' rights application directly from the Inventor.

BACKGROUND OF THE INVENTION

The present invention relates to a new and distinct cultivar of *Hebe*, botanically of hybrid origin, known as 'HM150255', and will be referred to hereafter by its cultivar name, 'HM150255'. 'HM150255' is an evergreen shrub grown for use as a container plant and as a landscape shrub.

The new cultivar was derived from a controlled breeding program conducted by the Inventor in Wezep, The Netherlands. The goal of the breeding program is to select new cultivars of *Hebe* with improved plant health, compact plant habits, small leaves, abundant flowering, and self-cleaning flowers. The new cultivar arose from a cross made in August of 2014 between an unnamed and unpatented proprietary plants from the Inventor's breeding program; reference no. H14-009 as the female parent and ref no. H13-005 as the male parent. The Inventor selected 'HM150255' in October 2015 as a single unique plant amongst the seedlings that resulted from the above cross.

Asexual propagation of the new cultivar was first accomplished by stem cuttings in August 2015 by the Inventor in Wezep, The Netherlands. Asexual propagation by stem cuttings and tissue culture using meristematic tissue has determined the characteristics of the new cultivar are stable and reproduced true to type in successive generations.

SUMMARY OF THE INVENTION

The following traits have been repeatedly observed and represent the characteristics of the new cultivar, which in combination distinguish 'HM150255' as a new and distinct cultivar of *Hebe*.

1. 'HM150255' exhibits consistently healthy plants that have a low susceptibility to leaf spot disease and downy mildew.
2. 'HM150255' exhibits strong stems.
3. 'HM150255' exhibits leaves that are small in size.
4. 'HM150255' exhibits flowers that are self-cleaning.
5. 'HM150255' exhibits flowers that are lavender-violet in color.
6. 'HM150255' exhibits a floriferous blooming habit.

The female parent of 'HM150255' differs from 'HM150255' in having a less compact plant habit, flowers that are less intense in color, leaves that are smaller in size, and in having more susceptibility to leaf spot disease and downy mildew. The male parent of 'HM150255' differs from 'HM150255' in having more susceptibility to leaf spot disease and downy mildew, a more vigorous growth habit, flowers that are less intense in color, and a longer flowering period. 'HM150255' can be most closely compared to the cultivars 'Autumn Glory' and 'Lowchi' (both un-patented). 'Autumn Glory' is similar to 'HM150255' in foliage color and flower color. 'Autumn Glory' differs from 'HM150255' in having a less compact plant habit, more susceptibility to leaf spot disease and downy mildew, and flowers that are less self-cleaning. 'Lowchi' is similar to 'HM150255' in having a compact plant habit and in consistently produces healthy plants with low susceptibility to leaf spot disease and downy mildew. 'Lowchi' differs from 'HM150255' in having inflorescences that are shorter in length, leaves that are more rounded in shape and blue-green in color, and flowers that are more blue in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by All-Blooms, cowellsgc, floraxchange, ozplanten, and Mouritsplants.

BRIEF DESCRIPTION OF THE DRAWINGS

The accompanying color photographs illustrate the overall appearance and distinct characteristics of the new *Hebe*. The photographs were taken of a 7-month-old plant of 'FSK17S28' as grown outdoors in a 12-cm container in Wezep, The Netherlands.

The photograph in FIG. 1 is a side view of 'HM150255' in bloom.

Figure 1:
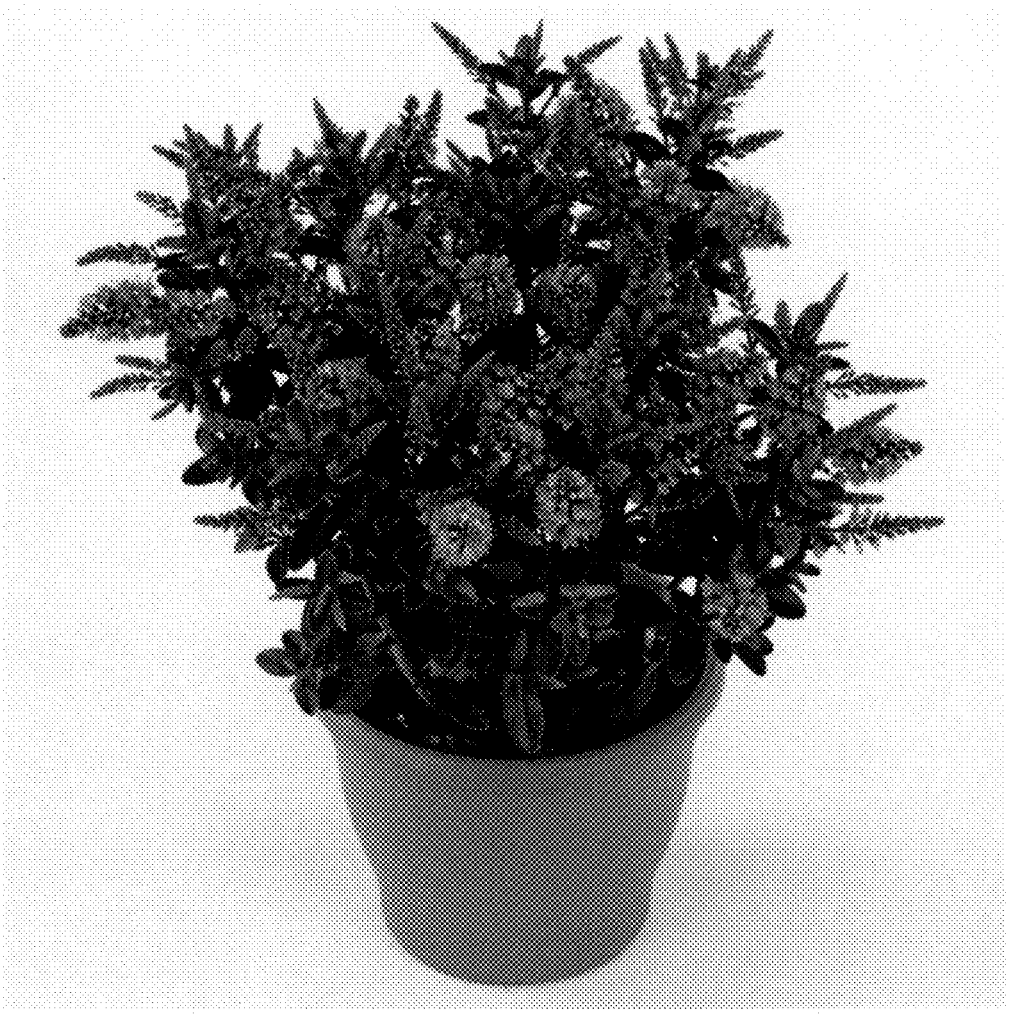
Figure 2:
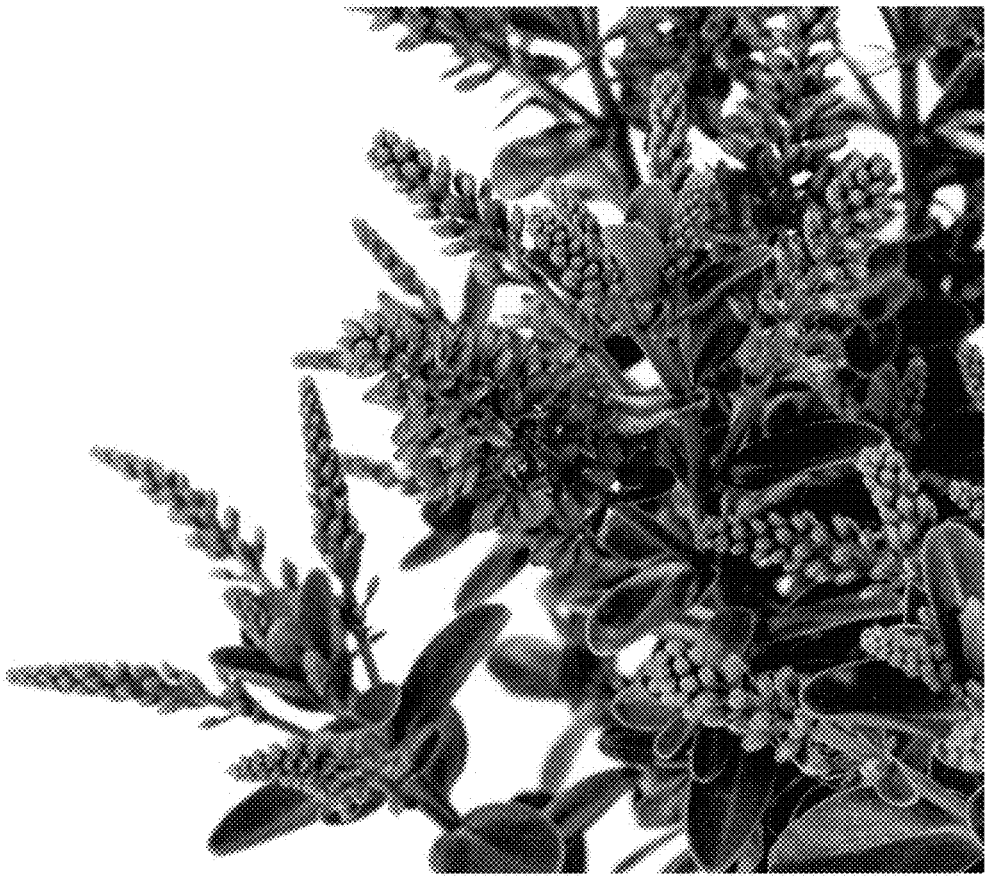

The photograph in FIG. 2 provides a close-up view of the inflorescences and foliage of 'HM150255'.

The colors in the photographs may differ slightly from the color values cited in the detailed botanical description, which accurately describe the colors of the new *Hebe*.

DETAILED BOTANICAL DESCRIPTION OF THE PLANT

The following is a detailed description of 7-month-old plants of the new cultivar as grown outdoors in 12-cm containers in Wezep, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—An average of 5 weeks from summer into autumn in the Netherlands.

*Plant type*.—Evergreen shrub.

*Plant habit*.—Compact.

*Height and spread*.—Average of 18 cm in height (soil level to top of foliar plane), 19.2 cm (soil level to top of floral plane) and 27.9 cm in spread as a 7-month-old plant, an average of 60 cm in height and spread as grown in the landscape.

*Cold hardiness*.—At least to U.S.D.A. Zone 8.

*Diseases and pests*.—Low susceptibility to leaf spot disease (*Septoria veronicae*) and downy mildew (*Perenospora* ssp.), no susceptibility or resistance to pests has been observed.

*Root description*.—Fibrous to slightly fleshy.

*Propagation*.—Softwood stem cuttings and tissue culture.

*Root development*.—3 to 4 weeks to initiate roots and 10 weeks to produce a young rooted plant.

*Growth rate*.—Moderate.

Branch description:

*Branch size*.—Lateral branches are an average of 17.4 cm in length and 3.25 mm in width.

*Branch shape*.—Round.

*Branch color*.—Young and mature; 146C, tinged 177B, internodes 144A, tinged 177C.

*Branch surface*.—Moderately glossy, densely covered with very short glandular hairs; 0.1 mm in length, matches surface color.

*Branch strength*.—Strong.

*Internode length*.—Average of 9.5 mm.

*Branching habit*.—Held in an average angle of 30° to vertical, average of 8 primary branches, 5 secondary branches.

Foliage description:

*Leaf shape*.—Ovate to elliptic, slightly carinate.

*Leaf division*.—Single.

*Leaf base*.—Cuneate.

*Leaf apex*.—Shallow retuse.

*Leaf venation*.—Pinnate; often with 3 main veins visible, upper surface; 146C, lower surface; 147B.

*Leaf margins*.—Entire, very slightly undulate.

*Leaf attachment*.—Sessile.

*Leaf arrangement*.—Opposite.

*Leaf surface*.—Both surfaces smooth, glabrous, non-rugose, moderately glossy.

*Leaf color*.—Young upper surface; 137A, margins 182B to 182C, young lower surface; 143A, mature upper surface; NN137A, mature lower surface; 146A.

*Leaf number*.—Average of 14 per lateral branch 17 cm in length.

*Leaf size*.—An average of 1.8 cm in length and 1.1 cm in width.

Flower description:

*Inflorescence type*.—Raceme.

*Inflorescence size*.—Average of 6.3 cm in height and 1.9 cm in width.

*Inflorescence lastingness*.—About 7 days, self-cleaning.

*Flower shape*.—Campanulate.

*Flower fragrance*.—None.

*Flower quantity*.—Average 40 florets per inflorescence, 1,000 flowers per plant, 5,000 flowers and flower buds per plant.

*Flower arrangement*.—Axillary racemes.

*Flower aspect*.—Outward.

*Flower size*.—Average of 7 mm in height, 6 mm in diameter, 7 mm in depth, throat diameter 1 mm, flower tube length 2 mm, flower tube diameter 1.75 mm.

*Peduncles*.—Strong strength, 5.7 cm in length and about 1.5 mm in diameter, 144A in color, held at about a 40° angle to lateral branch, surface is very slightly glossy and densely covered with very short glandular hairs; an average of 0.1 mm in length, color matches surface color.

*Pedicels*.—Moderately strong strength, average of 2 mm in length and 0.5 mm in diameter, held at about a 45° angle to peduncle, 146C in color, surface is very matte and densely covered with very short glandular hairs; an average of 0.1 mm in length, color matches surface color.

*Flower buds*.—Narrow oblong to narrow elliptic, 5 mm in length and 2 mm in diameter, color; 86B to 86D, immature calyx 138B, surface is matte, smooth and glabrous.

*Calyx*.—Rotate-shaped, average of 2 mm in length and diameter.

*Sepals*.—4, 1 whorl, 2 mm in length, 1 mm in width, elliptic in shape, entire margins, arrangement; rotate, acute tip, base cuneate and fused, surfaces dull and smooth, color: when opening and fully open upper and lower surface; 138B.

*Petals*.—Average 4, 1 whorl, upper petal and lateral petals obovate, lower petal narrow obovate, lower $1/3^{rd}$ of petals fused, 6 mm in length and 2.5 mm in width, entire and very slightly concave margins, apex obtuse, upper and lower surface is smooth and glabrous, non-rugose, both surfaces very slightly glossy, color: upper surface when opening; 86C, lower surface when opening; N87D, margins N87A, upper surface when fully open; a blend of 86D and N88D, margins N88D, lower surface when fully open; 85D, margins a blend of 86B and N87A.

*Floral bracts*.—A single bract is placed below each individual flower, narrow ovate in shape, tip acute, cuneate base, 1.5 mm in length, 0.75 mm in width, both surfaces glabrous and 138B in color.

Reproductive organs:

*Gynoecium*.—Pistil; 1, 5 mm in length, stigma; club-shaped, 5 mm in length, N79A in color, style; 5 mm in length and N79D in color, ovary; 143C in color.

*Androecium*.—Stamens: 2, anthers; oblong in shape, 1 mm in length, 0.5 mm in width and 175D in color, filaments; 4 mm in length, color; 85C to 85D, pollen; none observed.

*Fruit and seed*.—None observed to date.

It is claimed:

1. A new and distinct cultivar of *Hebe* plant named 'HM150255' as herein illustrated and described.

* * * * *